United States Patent [19]

Dewaele

[11] 4,110,323
[45] Aug. 29, 1978

[54] CONVERSION OF 2-DIALKYLAMINO-3H-AZEPINES INTO EPSILON CAPROLACTAMS

[75] Inventor: Sylvain A. R. Dewaele, Evergem, Belgium

[73] Assignee: s.a. Texaco Belgium n.v., Brussels, Belgium

[21] Appl. No.: 741,838

[22] Filed: Nov. 15, 1976

[30] Foreign Application Priority Data

Nov. 19, 1975 [GB] United Kingdom ...... 47581/75

[51] Int. Cl.$^2$ .......................................... C07D 201/02
[52] U.S. Cl. ............................................. 260/239.3 A
[58] Field of Search ................................. 260/239.3 A

[56] References Cited

PUBLICATIONS

Huisgen et al., Chemische Berichte, vol. 91(1), (1958) p. 1–12.

*Primary Examiner*—Henry R. Jiles
*Assistant Examiner*—Bernard Dentz
*Attorney, Agent, or Firm*—Thomas H. Whaley; Carl G. Ries; Bernard Marlowe

[57] ABSTRACT

This invention relates to a process of catalytically converting nitrobenzene to 2-amino-3H-azepines by the reaction of the nitrobenzene with trisaminophosphine and an amine of the formula HNR'$_2$, where R' is lower alkyl containing 1 to 6 carbon atoms.

In addition, this invention concerns the catalytic hydrogenation of 2-amino-3H-azepine to epsilon caprolactam.

2 Claims, No Drawings

CONVERSION OF 2-DIALKYLAMINO-3H-AZEPINES INTO EPSILON CAPROLACTAMS

This invention concerns a method for the production of ε-caprolactams, and especially of ε-caprolactam itself. It is particularly suitable for the production of ε-caprolactam from nitrobenzene.

ε-caprolactam is the monomer of polycaprolactam, or nylon-6. This polyamine is widely used for such diverse purposes as tire cord, fishing line, ropes, hosiery and woven and knitted fabrics. ε-caprolactam is generally manufactured by the Beckmann rearrangement of cyclohexanone oxime, which can itself be produced by a variety of methods including (a) the hydrogenation of phenol followed by the partial dehydrogenation of the resulting cyclohexanol to give cyclohexanone, which is converted into its oxime; (b) hydrogenation of aniline to give cyclohexylamine which is converted directly into cyclohexanone oxime by treatment with hydrogen peroxide; and (c) the photochemical reaction of cyclohexane with nitrosyl chloride in the presence of hydrogen chloride to give cyclohexanone oxime hydrochloride directly.

None of the above-mentioned processes is without its disadvantages, and some of them involve a considerable number of process stages. There is a clear need for simpler processes, requiring less capital investment and less expensive chemical operation.

Huisgen, Vossius and Appl described in Chem. Ber., 91, 1 (1958) discloses the hydrogenation of 2-anilino-3H-azepine to their tetrahydroderivative 2-anilino-3H-tetrahydroazepine which was then hydrolyzed to ε-amino caproic acid.

Another seemingly relevant disclosure of the prior art is Cadogen et al [Journal Chem. Soc. - London (C), 1969, 2808] who described the conversion of nitrobenzene with $CH_3P(OEt)_2$ in $(C_2H_5)_2NH$. However, the process is disadvantageous in that it takes up to 5 days for the conversion shown below:

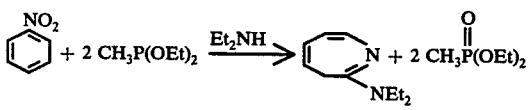

It has now been found that it is possible to convert certain 2-amino-3H-azepines directly into ε-caprolactam.

One facet of the present invention provides a method for the production of ε-caprolactams of the formula

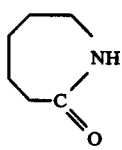

(I)

which comprises catalytically hydrogenating, in an aqueous inert solvent mixture, a 2-amino-3H-azepine derivative of the general formula:

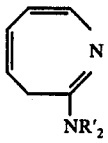

(II)

in which each R' represents an alkyl group containing 1 to 6 carbon atoms.

The 2-amino-3H-azepines of formula II are compounds which are themselves either unknown or not widely available. It has been found, however, that they can be obtained in a simple one-stage process by reacting a nitrobenzene of the formula

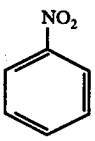

(III)

with a trisaminophosphine of the formula $(R'_2N)_3P$         (IV)

and an amine of the formula $H—NR'_2$

In this formula R' has the meaning given above.

The 2-amino group $NR'_2$ is preferably a dibutylamino group. It may however be another dialkylamino group (e.g. dimethylamino, diethylamino or dipropylamine).

The 2-amino-3H-azepine(II) can be prepared by reacting the nitrobenzene(III) with a trisaminophosphine (IV). The reaction conditions for this rearrangement are not critical and, in general, temperatures up to 200° C. can be employed. A reaction temperature of 150° C. is convenient. The reaction is preferably carried out at atmospheric pressure. Since the preferred azepine is 2-dibutylamino-3H-azepine(V), the preferred trisaminophosphine is tris(dibutylamino) phosphine(VI).

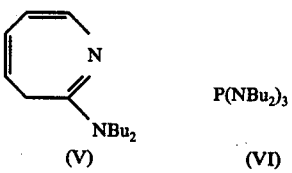

(V)         (VI)

According to a preferred embodiment of the invention, the trisaminophosphine can be prepared in situ by reacting phosphorus trichloride with an appropriate secondary amine, preferably dibutylamine. This reaction can be carried out in a solvent, e.g. diethyl ether and preferably at least 6 moles of the secondary amine are added, in accordance with the equation $PCl_3 + 6 HNR'_2 \rightarrow (R'_2N)_3P + 3 HNR'_2 \cdot HCl$.

Reaction between the secondary amine and phosphorus trichloride can, if desired, be carried out in the presence of inert solvent, and in many instances it is preferred to employ an inert solvent in these reactions. Suitable solvents include diethyl ether and hexane. Where inert solvent is used, it should be one in which the amine hydrochloride, formed in the above reaction, is insoluble. It is necessary to use inert solvent when dibutylamine is reacted with phosphorus trichloride.

Conversion of the nitrobenzene(III) into the azepine-(II) is advantageously carried out in the presence of an excess of the secondary amine, which can be used as solvent. This reaction is conveniently carried out by boiling under reflux and follows the reaction scheme:

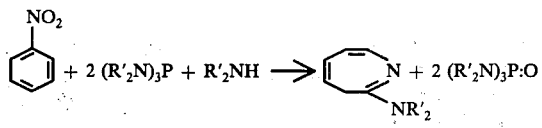

The hydrogenation of the azepine(II) to the ε-caprolactam(I) is carried out in an aqueous-inert, solvent system containing about 5% by weight water in the presence of a catalyst, most advantageously a Group VIII metal catalyst. The solvent system can comprise any suitable solvent for the azepine. Ethanol is generally preferred. Sufficient water must be present for hydrolysis of the initially formed enamine hydrogenation product but too much water should not be used. It is generally convenient to carry out the reaction in an alkanol such as ethanol containing about 5% by weight water.

Reaction can be carried out under a variety of temperatures and pressures. It is generally preferred at a temperature of from 0° to 75° C, most preferably at about room temperature. The preferred pressure is atmospheric pressure, but higher pressures up to the safety limit for the apparatus, e.g., up to 200 atmospheres, can be employed if desired. It is important, however, to avoid such a combination of high temperatures and pressures as would bring about hydrogenation of the double bond in the grouping

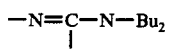

A Group VIII metal catalyst is generally employed in the hydrogenation. Suitable catalysts include Raney nickel, Adam's catalyst (PtO$_2$) and palladium or platinum on a suitable substrate, such as charcoal, silica, asbestos, barium sulphate or calcium carbonate. 5% by weight palladium on calcium carbonate can conveniently be used.

After hydrogenation, the ε-caprolactam can be separated from the catalyst, e.g. by filtering or decanting, and then from the solvent, e.g. by evaporation or by pouring the solution into a non-solvent for caprolactam, followed by filtration or a further solvent extraction.

The invention is further illustrated by the following non-limiting examples.

EXAMPLE 1

A solution of 68.7 g (0.5 mole) of phosphorus trichloride in dry hexane or diethyl ether is added slowly to a stirred solution of 363.6 g (3.0 moles) of dibutylamine in the same solvent. A voluminous precipitate of dibutylamine hydrochloride is formed, the temperature remaining between 10° and 40° C. After all the phosphorus trichloride has been added, the mixture is boiled and refluxed for between 30 minutes and 2 hours. The mixture is then cooled to room temperature and filtered to separate it from 280 g (1.7 moles) of dibutylamine hydrochloride. The solvent is then stripped off at reduced pressure in a rotary evaporator.

A further 335.4 g (2.4 moles) of dibutylamine is added to the residue, followed by 12.3 g (0.1 mole) of nitrobenzene. The resulting mixture is heated at 150° C. under dry nitrogen, while stirring, for a period from 1 to 4 hours. The consumption of nitrobenzene is followed by gas chromatography. Once reaction is complete, excess dibutylamine is evaporated at 88° C./70 mm Hg. and the residue is separated into its components by distillation.

2-dibutylamino-3H-azepine, b.p. 98° C./0.001 mm Hg is obtained in 55% yield. Tris-dibutylaminophosphine (b.p. 138° C./0.003 mm Hg) and phosphoric acid tris-(dibutylamide) (b.p. 142°-144° C./0.06 mm Hg) are also present in the residue. In related runs dipropylamine and diethylamine are substituted for dibutylamine on a mole for mole basis to produce the corresponding 2-dipropylamino-3H-azepine and 2-diethylamine-3H-azepine respectively.

EXAMPLES 2 TO 4

Following the procedure generally set out in Example 1, 2-dibutylamino-3H-azepine is obtained from phosphorus trichloride, dibutylamine and nitrobenzene, using hexane in Examples 3 and 4 and diethyl ether in Example 2.

The quantities of reactants, the reaction time at 150° C, and the yield of 2-dibutylamino-3H-azepine are set out below in the Table.

TABLE

| Example | Phosphorus Trichloride | | Dibutylamine | | Nitrobenzene | | Solvent | Time | Yield |
|---|---|---|---|---|---|---|---|---|---|
| | g. | mole | g. | mole | g. | mole | ml. | hr. | % |
| 2 | 34.4 | 0.25 | 347.1 | 2.7 | 6.1 | 0.05 | A/900 | 3 | 61.7 |
| 3 | 301.2 | 2.2 | 1815 | 14.0 | 90.0 | 0.73 | B/5000 | 1.5 | 54.1 |
| 4 | 301.2 | 2.2 | 1816 | 14.0 | 90.2 | 0.73 | B/4000 | 4 | 57.7 |

A = dietyl ether,
B = hexane.

EXAMPLE 5

A solution of 5.45 g (0.25 moles) of 2-dibutylamino-3H-azepine in 45 ml of ethanol containing 5% of water was hydrogenated in the presence of 1.0 g of a 5% palladium on calcium carbonate catalyst. After 17 days, the total uptake of hydrogen is 1520 ml (theoretical uptake = 1200 ml).

Filtration and evaporation of the solvent, followed by distillation of the residue give 2.34 g (84% of theory) of ε-caprolactam, (b.p. 95°-133.5° C./0.017 mm Hg; m.p. 59.5°-69.5° C.).

EXAMPLE 6

A solution of 20 g (0.091 moles) of 2-dibutylamino-3H-azepine in 120 ml of 5% aqueous ethanol is hydrogenated in the presence of 7 g of Raney nickel. After 31 hours, the uptake of hydrogen is 3300 ml, compared with a theoretical uptake of 4337 ml. A further 8.4 g of Raney nickel is added and hydrogenation is continued for a further 7 hours, after which time a further 1242 ml of hydrogen has taken up. After working up as in Example 5, ε-caprolactam is obtained in a yield of 9.5 g (92.5% of theory).

What is claimed is:

1. A process for preparing epsilon caprolactams from 2-N,N-dialkylamino-3H azepines wherein the alkyl substituents contain from 1 to 6 carbon atoms, by the steps of:

(a) mixing each mole of said azepine to be hydrogenated, at 20°–30° C, with a solubilizing amount of 95% by weight of deoxygenated alkanol, to form a hydrogenation mixture.

(b) in the presence of between 0.1 to 5% by weight of a Group VIII (a) metal catalyst, said catalyst being selected from the group consisting of Raney nickel, Adam's catalyst and platinum or palladium on a solid-inert support.

(c) passing hydrogen gas through said hydrogenation mixture at 0° to 75° C, at atmospheric to 200 atmospheres of hydrogen until epsilon caprolactam is formed.

2. The process of claim 1 wherein the azepine hydrogenated is 2-dibutylamino-3H-azepine.

* * * * *